(12) United States Patent
Chau et al.

(10) Patent No.: US 7,749,177 B2
(45) Date of Patent: *Jul. 6, 2010

(54) APPARATUS AND METHOD FOR DETECTING ASPIRATION

(75) Inventors: Thomas T. K. Chau, Toronto (CA); David J. Kenny, Toronto (CA); Michael J. Casas, Toronto (CA); Glenn Berall, Toronto (CA)

(73) Assignee: Bloorview Kids Rehab, Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/401,505

(22) Filed: Mar. 10, 2009

(65) Prior Publication Data

US 2009/0227908 A1 Sep. 10, 2009

Related U.S. Application Data

(62) Division of application No. 10/869,024, filed on Jun. 17, 2004, now abandoned.

(51) Int. Cl.
*A61B 5/103* (2006.01)
*A61B 5/117* (2006.01)
(52) U.S. Cl. ...................................... 600/593
(58) Field of Classification Search ................ 600/561, 600/587, 593; 607/39–40, 62, 72, 118
See application file for complete search history.

(56) References Cited

U.S. PATENT DOCUMENTS 5,024,240 A * 6/1991 McConnel .................. 600/593

| 5,143,087 A | | 9/1992 | Yarkony |
| 5,263,491 A | | 11/1993 | Thornton |
| 5,363,858 A | * | 11/1994 | Farwell ..................... 600/544 |
| 5,445,144 A | * | 8/1995 | Wodicka et al. ........ 128/207.14 |
| H1557 H | | 7/1996 | Joubert et al. |

(Continued)

FOREIGN PATENT DOCUMENTS

WO WO0226101 4/2002

(Continued)

OTHER PUBLICATIONS

U.S. Appl. No. 10/869,024—Advisory Action Before the Mailing of an Appeal Brief; Jan. 19, 2007.

(Continued)

*Primary Examiner*—Max Hindenburg
*Assistant Examiner*—Rene Towa
(74) *Attorney, Agent, or Firm*—Benesch, Friedlander, Coplan & Aronoff LLP

(57) ABSTRACT

An apparatus and method for detecting swallowing activity is provided. In an embodiment, a method includes receiving an electronic signal from an accelerometer that represents swallowing activity, extracting at least two features from the signal, classifying the signal as a type of swallowing activity based on the extracted features, and generating an output of the classification. Exemplary activities include swallows, aspirations, movement and vocal artifacts. By indicating whether an activity is a swallow or an aspiration, the manner in which a patient afflicted with an increased likelihood for aspirations is fed can be adjusted to increase the likelihood of achieving a swallow instead of an aspiration during feeding. In turn this could reduce hospitalizations for aspiration pneumonia in patients with acute or chronic injury.

26 Claims, 4 Drawing Sheets

U.S. PATENT DOCUMENTS

| | | | |
|---|---|---|---|
| 5,891,185 | A | 4/1999 | Freed et al. |
| 5,970,978 | A * | 10/1999 | Aviv et al. ............. 128/207.14 |
| 6,267,729 | B1 | 7/2001 | Addington et al. |
| 6,383,142 | B1 * | 5/2002 | Gavriely ..................... 600/529 |
| 6,445,942 | B1 * | 9/2002 | Berthon-Jones et al. ..... 600/407 |
| 6,463,328 | B1 * | 10/2002 | John ............................ 607/45 |
| 6,568,397 | B1 | 5/2003 | Addington et al. |
| 6,581,605 | B2 | 6/2003 | Addington et al. |
| 6,978,787 | B1 * | 12/2005 | Broniatowski .............. 128/898 |
| 2002/0133194 | A1 | 9/2002 | Leelamanit et al. |
| 2003/0018276 | A1 * | 1/2003 | Mansy et al. ................ 600/529 |
| 2003/0073920 | A1 * | 4/2003 | Smits et al. .................. 600/544 |

FOREIGN PATENT DOCUMENTS

| | | |
|---|---|---|
| WO | WO02082968 | 10/2002 |
| WO | WO2004011035 | 2/2004 |
| WO | WO2005023105 | 3/2005 |

OTHER PUBLICATIONS

U.S. Appl. No. 10/869,024—Interview Summary; Jul. 10, 2007.
U.S. Appl. No. 10/869,024—Interview Summary; Aug. 28, 2006.
U.S. Appl. No. 10/869,024—Interview Summary; Dec. 8, 2006.
U.S. Appl. No. 10/869,024—Office Action; May 23, 2006.
U.S. Appl. No. 10/869,024—Office Action; May 29, 2008.
U.S. Appl. No. 10/869,024—Office Action; Sep. 12, 2007.
U.S. Appl. No. 10/869,024—Office Action; Nov. 1, 2006.
U.S. Appl. No. 10/869,024—Office Action; Dec. 10, 2008.
Lim, Lieu, Phua, Seshadri, Venketasubramanian, Lee and Choo, "Accuracy of Bedside Clinical Methods Compared with Fibersoptic Endoscopic Examination of Swallowing (FEES) in Determining the Risk of Aspiration in Acute Stroke Patients", Dysphagia, 16:1-6 (2001), Springer-Verlag New York Inc.
Sellars, Dunnet and Carpenter, "A Preliminary Comparison of Videofluoroscopy of Swallow and Pulse Oximetry in the Identification of Aspiration of Dysphagic Patients", Dysphagia, 13:82-86 (1998), Springer-Veriag New York Inc.
Mayo Clinic Website: (1) "Treatment of Aspiration"; and (2) "Frequently Asked Questions about Swallowing", Jacksonville, Florida, Oct. 12, 2003.
Sherman, Nisenboum, Jesberger, Morrow and Jesberger, "Assessment of Dysphagia with the Use of Pulse Oximetry", Dysphagiam 14:152-156 (1999), Springer-Veriag New York Inc.
Casas, M.J., Kenney, D.J., Chau, T., and Berall, G., PowerPoint Presentation "Characterization of Pediatric Aspiraion Sounds", Jun. 2002.
Martin-Harris, Logemann, McMahon, Schleicher and Sandidge, "Clinical Utility of the Modified Barium Swallow", Dysphagia, 15:136-141 (2000), Springer-Veriag New York Inc.
Madden, Fenton, Hughes and Timon, "Comparison between videofluoroscopy and milk-swallow endoscopy in the assessment of swallowing function", Clin, Otolaryngol, 2000, 25, 504-506, Blackwell Science Ltd.
Colodny, "Comparison of Dysphagics and Nondysphagics on Pulse Oximetry during Oral Feeding", Dysphagia, 15:68-73 (2000), Springer-Veriag New York Inc.
Silva and Chau, "Coupled microphone-accelerometer sensor pair for dynamic noise reduction to MMG signal recording", Electronics Letters, Oct. 16, 2003, vol. 39, No. 21.
Cichero and Murdoch, "Detection of Swallowing Sounds: Methodology Revisited", Dysphagia, 17:40-49 (2002), Springer-Veriag New York Inc.
Sonles, B.C. (1994). "Dysphagia: A model for differential diagnosis for adults and children." In L.R. Chemey (Ed.) Clinical Management of Dysphagia in Adults and Children 2nd edition, Gaithersburg, M: Aspen Publishers Inc.
Leder, Sasaki and Burrell, "Fiberoptic Endoscopic Evaluation of Dysphagia to Identify Silent Aspriation", Dysphagia, 13:19-21 (1998), Springer-Veriag new York Inc.
Leder and Karas, "Fiberoptic Endoscopic Evaluation of Swallowing in Pediatric Population", The Laryngoscope, 110: Jul. 2000, 1132-1136, Lippincott Williams & Wilkins, Inc., Philadelphia, USA.
Das, Reddy, and Narayanan, "Hybrid fuzzy logic committee neutral networks for recognition of swallow acceleration signals", Computer Methods and Programs in Biomedicine, 64 (2001) 87-99, Elsevier Science ireland Ltd.
Stroud A.E., Lawrie, B.W., & Wiles, C.M. (2002). "Inter-and intra-rater reliability of cervical auscultation to detect aspiration in patients with dysphagia." Clinical Rehabilitation, 16, 6, 640-645.
Miyazaki, Arakawa and Kizu, "Introduction of Simple Swallowing Ability Test for Prevention of Aspiration Pneumonia in the Elderly and Investigation of Factors of Swallowing Disorders", 122(1) 97-105 (2002), The Pharmaceutical Society of Japan.
Reddy, Katakam, Gupta, Unnikrishnan, Narayanan and Canilang, "Measurement of acceleration during videofluorographic evaluation of of dysphagic patients", Medical Engineering & Physics; 22 (2000) 405-412, Elsevier Science Ireland Ltd.
Beck, T.J., & Gayler, B.W. (1991). "Radiation in video-recorded fluoroscopy." In B. Jones & M.W. Donner (Eds.) Normal and Abnormal Swallowing: Imaging in Diagnosis and Therapy. Springer-Veriag.
Chau, Casas, Berall and Kenney, Poster Presentation, "To characterize normality and stationarity properities of pediatric aspiration signals", Houston, Texas, Oct. 2002.
The Neuroscience on the Web Series: SPPA 342, Neuropathologies of Swallowing and Speech, CSU, Chico and McCaffrey, Unit 5. The Nature of the Swallow, Oct. 12, 2003.
Scott, Perry and Bench, "A Study of Interrater Reliability when Using Videofluoroscopy as an Assessment of Swallowing", Dysphagia, 13:223-227 (1998), Springer-Veriag New York Inc.
Chau T. et al., Testing the Stationary and Normality of Pediatric Aspiration Signals, Proceedings of the Second Joint EMBS/BMES Conference, Oct. 2002, pp. 186-187, Houston, TX, USA.
Reddy, Thomas, Canilang and Casterline, "Toward classification of dysphagic patients using biomechanical measurements", Journal of Rehabilitation Research and Development, vol. 31 No. 4, Nov. 1994, pp. 335-344, Department of Veterans Affairs.
Leder, "Use of Arterial Oxygen Saturation, Heart Rate, and Blood Pressure as Indirect Objective Physiologic Markers to Predict Aspiration", Dysphagia, 15:201-205 (2000), Springer-Veriag New York Inc.
Zenner, Losinski and Mills, "Using Cervical Auscultation in the Clinical Dysphagia Examination in Long-Term Care", Dysphagia, 10:27-31 (1995), Springer-Veriag New York Inc.
Wright, R.E.R., Wright F.R., & Carson, C.A. (1996). "Videofluoroscopic assessment in children with severe cerebral palsy presenting with dysphagia." Pediatric Radiology, 26, 10, 720-722.
The Voice and Swallowing Center website: (1) "Frequently Asked Questions"; and (2) "What's Considered a Swallowing Problem?", College of Physicians & Surgeons, Columbia University, Oct. 12, 2003.
Laubert, "Zur Diagnostik der postoperativen Dysphagle und Aspiration, Fiberoptisch-endoskopisch kontrollerter Methylen-Blauschiuck", HNO, May 1999, pp. 479-484, Springer-veriag New York Inc.

* cited by examiner

APPARATUS AND METHOD FOR DETECTING ASPIRATION

CROSS REFERENCE TO RELATED APPLICATIONS

This application is a divisional of U.S. application Ser. No. 10/869,024 filed on Jun. 17, 2004, the disclosure of which is incorporated by reference herein in its entirety.

FIELD OF THE INVENTION

The present invention relates generally to the diagnosis of aspiration and more particularly relates to an apparatus and method for detecting swallowing and related activity.

BACKGROUND OF THE INVENTION

Dysphagia refers to any deglutition (swallowing) disorder, including abnormalities within the oral, pharyngeal and esophageal phases of swallowing. Dysphagia is common in individuals with neurological impairment, due to, for example, cerebral palsy, cerebrovascular accident, brain injury, Parkinson's disease, stroke and multiple sclerosis. Individuals with dysphagia are often at risk of aspiration. Aspiration refers to the entry of foreign material into the airway during inspiration. Aspiration may manifest itself in a number of different ways. The individual may begin to perspire and the face may become flushed. Alternatively, the individual may cough subsequent to swallowing. In silent aspiration, there are no overt clinical or easily recognizable signs of bolus inhalation. The invention is particularly useful for individuals with silent aspiration, but is also applicable for other manifestations of aspiration. Aspiration bears serious health consequences such as chronic lung disease, aspiration pneumonia, dehydration, and malnutrition.

Dysphagia afflicts an estimated fifteen million people in the United States. Certain sources indicate that fifty thousand people die each year from aspiration pneumonia (Dray et al., 1998). The occurrence of diffuse aspiration bronchiolitis in patients with dysphagia is not uncommon, regardless of age (Matsuse et al., 1998). Silent aspiration is especially prominent in children with dysphagia, occurring in an estimated 94% of that population (Arvedson et al., 1994). Half of stroke survivors have swallowing difficulties (Zorowitz & Robinson, 1999), which translates to 500,000 people per year in the United States, (Broniatowski et al., 2001), and aspiration is reported in 75% of these cases while 32% report chest infections (Perry & Love, 2001). The incidence of dysphagia is particularly significant in acute care settings (25-45%), chronic care units (50%) (Finiels et al., 2001) and homes for the aged (68%) (Steele et al., 1997). Dysphagia tremendously diminishes quality of life for people of all ages, compromising not only medical, but social, emotional and psychosocial well-being.

The modified barium swallow using videofluoroscopy is the current gold standard for confirmation of aspiration (Wright et al., 1996). Its clinical utility in dysphagia management continues to be asserted (e.g., Martin-Harris, 2000; Scott et al., 1998). The patient ingests barium-coated material and a video sequence of radiographic images is obtained via X-radiation. The modified barium swallow procedure is invasive and costly both in terms of time and labor (approximately 1,000 health care dollars per procedure in Canada), and renders the patient susceptible to the effects of ionizing radiation (Beck & Gayler, 1991).

Fibreoptic endoscopy, another invasive technique in which a flexible endoscope is inserted transnasally into the hypopharynx, has also been applied in the diagnosis of postoperative aspiration (Brehmer & Laubert, 1999) and bedside identification of silent aspiration (Leder et al., 1998). Fibreoptic endoscopy is generally comparable to the modified barium swallow in terms of sensitivity and specificity for aspiration identification (e.g., Madden et al., 2000; Leder & Karas, 2000), with the advantage of bedside assessment.

Pulse oximetry has been proposed as a non-invasive adjunct to bedside assessment of aspiration (e.g., Sherman et al., 1999; Lim et al., 2001). However, several controlled studies comparing pulse oximetric data to videofluoroscopic (Sellars et al., 1998) and fiberoptic endoscopic evaluation (Leder, 2000; Colodny, 2000) have raised doubts about the existence of a relationship between arterial oxygen saturation and the occurrence of aspiration.

Cervical auscultation involves listening to the breath sounds near the larynx by way of a laryngeal microphone, stethoscope or accelerometer (Zenner et al., 1995) placed on the neck. It is generally recognized as a limited but valuable tool for aspiration detection and dysphagia assessment in long-term care (Zenner et al., 1995; Cichero & Murdoch, 2002; Stroud et al., 2002). However, when considered against the gold standard of videofluoroscopy, bedside evaluation even with cervical auscultation yields limited accuracy (40-60%) in detecting aspirations (Sherman et al., 1999; Selina et al., 2001; Sellars et al., 1998). Indeed, our recent research shows that aspirations identified by clinicians using cervical auscultation, represent only a quarter of all aspirations (Chau, Casas, Berall & Kenny, submitted).

Swallowing accelerometry (Reddy et al., 2000) is closely related to cervical auscultation, but has entailed digital signal processing and artificial intelligence as discrimination tools, rather than trained clinicians. In clinical studies, accelerometry has demonstrated moderate agreement with videofluoroscopy in identifying aspiration risk (Reddy et al., 1994) where as the signal magnitude has been linked to the extent of laryngeal elevation (Reddy et. al, 2000). Recently, fuzzy committee neural networks have demonstrated extremely high accuracy at classifying normal and "dysphagic" swallows (Das et al., 2001). However, prior art swallowing accelerometry only provides limited information in classifying normal from "dysphagic" swallows and does not provide broader information about the clinical status of the patient.

Administration of videofluoroscopy or nasal endoscopy requires expensive equipment and trained professionals such as a radiologist, otolaryngologist or speech-language pathologist (Sonies, 1994). Invasive procedures are not well-tolerated by children and cannot be practically administered for extended periods of feeding. There is a need for an economical, non-invasive and portable method of aspiration detection, for use at the bedside and outside of the institutional setting.

SUMMARY OF THE INVENTION

It is an object of the present invention to provide a novel apparatus and method for detecting swallowing activity that obviates or mitigates at least one of the above-identified disadvantages of the prior art.

An aspect of the invention provides a method for detecting swallowing activity comprising the steps of:
 receiving an electronic signal representing swallowing activity;
 extracting at least two features from the signal;
 classifying the signal as a type of swallowing activity based on the features; and,
 generating an output representing the classification.

The electronic signal can be generated by an accelerometer. The features can include at least one of stationarity, normality and dispersion ratio. The classifying step can be performed using a radial basis neural network.

The swallowing activity can include at least one of a swallow and an aspiration.

The extracting step can include stationarity as one of the features, the extracting step of stationarity including the following sub-steps:
- dividing the signal into a plurality of non-overlapping bins;
- determining a total number of total number of reverse arrangements, ($A_{Total}$) in a mean square sequence is determined;
- extracting the stationarity feature (z), determined according to the following equation:

$$z = \frac{A_{Total} - \mu_A}{\sigma_A}$$

where:
$\mu_A$ is the mean number of reverse arrangements expected for a stationary signal of the same length.
$\sigma_A$ is the standard deviation for an equal length stationary signal Each of the bins can be between about one ms and about nine ms in length. Each of the bins can be between about three ms and about seven ms in length. Each of the bins can be about five milliseconds ("ms") in length.

The extracting step can include normality as one of the features, the extracting step of normality including the following sub-steps:
- standardizing the signal to have zero mean and unit variance ("s").
- dividing the standardized signal into a plurality of bins ("l") each of about 0.4 Volts, where $$\left\lceil \frac{\max(s) - \min(s)}{0.4} \right\rceil,$$

and wherein a highest bin extends to infinity and a lowest bin extends to negative infinity.
- determining observed frequencies ("n") for each the bin by counting the number of samples in the standardized signal ("s") that fell within each the bin.
- determining expected frequencies $\hat{m}$ for each the bin is determined under the assumption of normality, using a Chi-square ($X^2$) statistic using the following:

$$\hat{X}^2 = \sum_{i=1}^{l} \frac{(n_i - \hat{m}_i)^2}{\hat{m}_i}$$

determining the normality feature using the following:

$$\log_{10}(\hat{X}^2)$$

The extracting step can include a dispersion ratio as one of the features, the extracting step of dispersion ratio including the following sub-steps:
- determining a mean absolute deviation of the signal according to the following:

$$S_1 = \frac{1}{n}\sum_{i=1}^{n}|x_i - med(x)|$$

- determining an interquartile range, $S_2$, of the signal
- extracting the dispersion ratio according to the following:

$$\frac{S_1}{S_2}$$

Another aspect of the invention provides a device for detecting swallowing activity comprising an input device for receiving an electronic signal from a sensor. The electronic signal can represent swallowing activity. The device also comprises a microcomputer connected to the input device that is operable to extract at least two features from the signal. The microprocessor is further operable to classify the signal as a type of swallowing activity based on the features. The device also includes an output device connected to the microcomputer for generating an output representing the classification.

BRIEF DESCRIPTION OF THE DRAWINGS

The invention will now be described by way of example only, and with reference to the accompanying drawings, in which.

DETAILED DESCRIPTION OF THE INVENTION

As used herein the terms "swallow" and "penetration" are distinguished from the term "aspiration". As used herein, a "swallow" is the safe passage of foodstuffs from the oral cavity, through the hypopharynx and into esophagus. Further, a swallow is accompanied by a period of apnea with no entry of foodstuffs into the protected airway. "Penetration" is the entry of foreign material into the airway but not accompanied by inspiration. However, an "aspiration" is the entry of foreign material into the airway during inspiration. As used in relation to the embodiments discussed below, the term "swallowing activity" means a swallow or an aspiration or the absence of either, but in other embodiments "swallowing activity" can refer to other types of activities including penetration.

Figure 1:
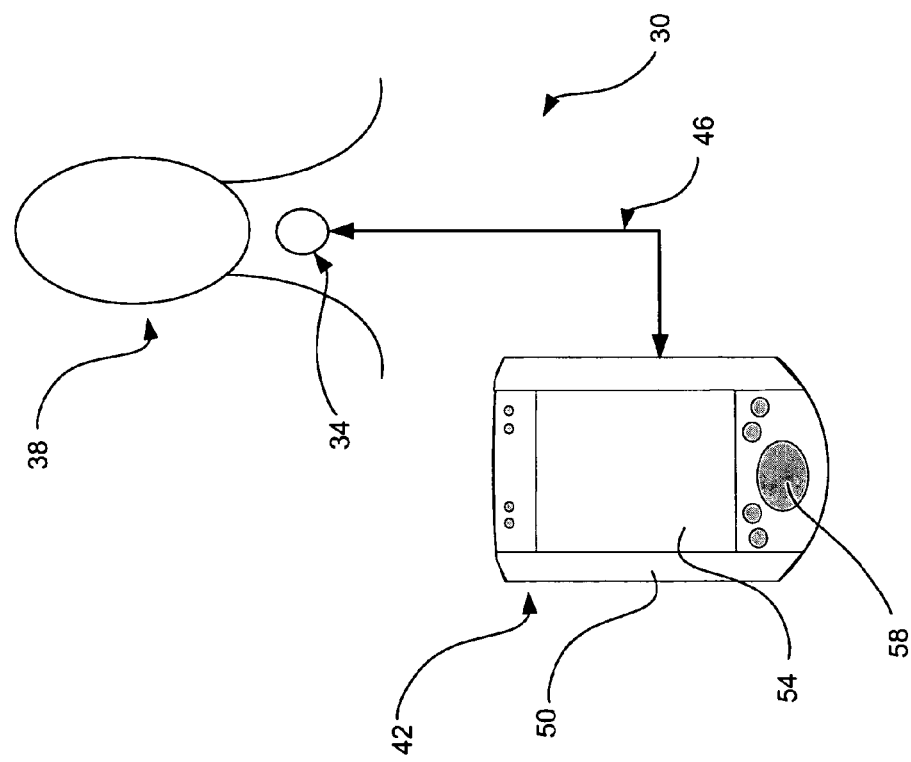
FIG. 1 is a schematic representation of an apparatus for detecting swallowing activity in accordance with an embodiment of the invention.

Referring now to FIG. 1, an apparatus for detecting swallowing activity is indicated generally at 30. Apparatus 30 includes an accelerometer 34 that is positioned on the throat of a patient 38. In a present embodiment, accelerometer 34 is placed infer-anterior to the thyroid notch, so that the axis of the accelerometer 34 is aligned to measure anterior-posterior vibrations. Apparatus 30 also includes a computing device 42 that is connected to accelerometer 34 via a link 46. Link 46 can be wired or wireless as desired and corresponding to appropriate interfaces on accelerometer 34 and device 42. Apparatus 30 is operable to receive acceleration signals from accelerometer 34 that reflect swallowing activity in patient 38.

In a present embodiment, accelerometer 38 is the EMT 25-C single axis accelerometer from Siemens Canada, Mississauga, Ontario Canada ("EMT 25-C"). Other accelerometers that can be used will occur to those of skill in the art.

In a present embodiment, computing device 42 is based on the computing environment and functionality of a personal digital assistant that includes a chassis 50 that frames a display 54 for presenting user output and a plurality of keys 58 for receiving user input. Computing device 42 thus includes an interface to allow device 42 to connect to accelerometer 34 via link 46. Computing device 42 thus includes any suitable arrangement of microprocessor, random access memory, non-volatile storage, operating system, etc. As will be explained in greater detail below, computing device 42 is operable to receive signals from accelerometer 34 and to detect swallowing activity from such signals, and report on those activities by presenting output on display 54.

Figure 2:
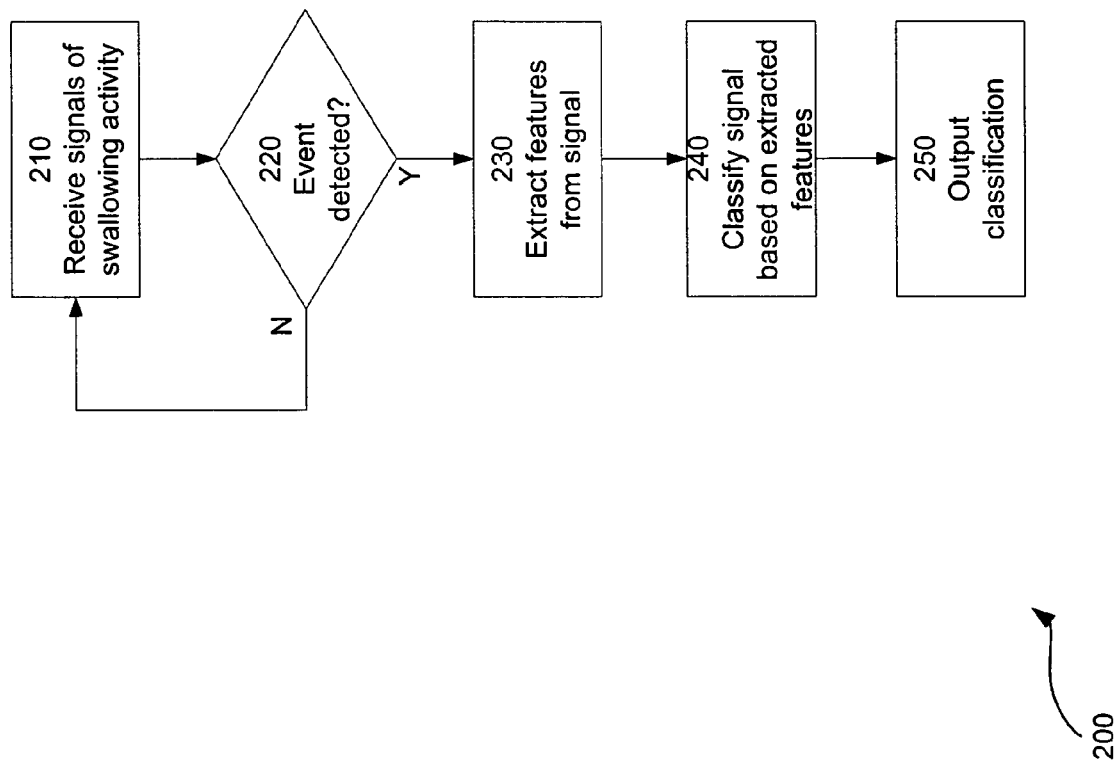
FIG. 2 is a flow chart depicting a method for detecting swallowing activity in accordance with another embodiment of the invention.

In order to help explain certain of these implementations and various other aspects of apparatus 30, reference will now be made to FIG. 2 which shows a method for detecting swallowing activity and which is indicated generally at 200. However, it is to be understood that apparatus 30 and/or method 200 can be varied, and need not work exactly as discussed herein in conjunction with each other, and that such variations are within the scope of the present invention.

Figure 3:
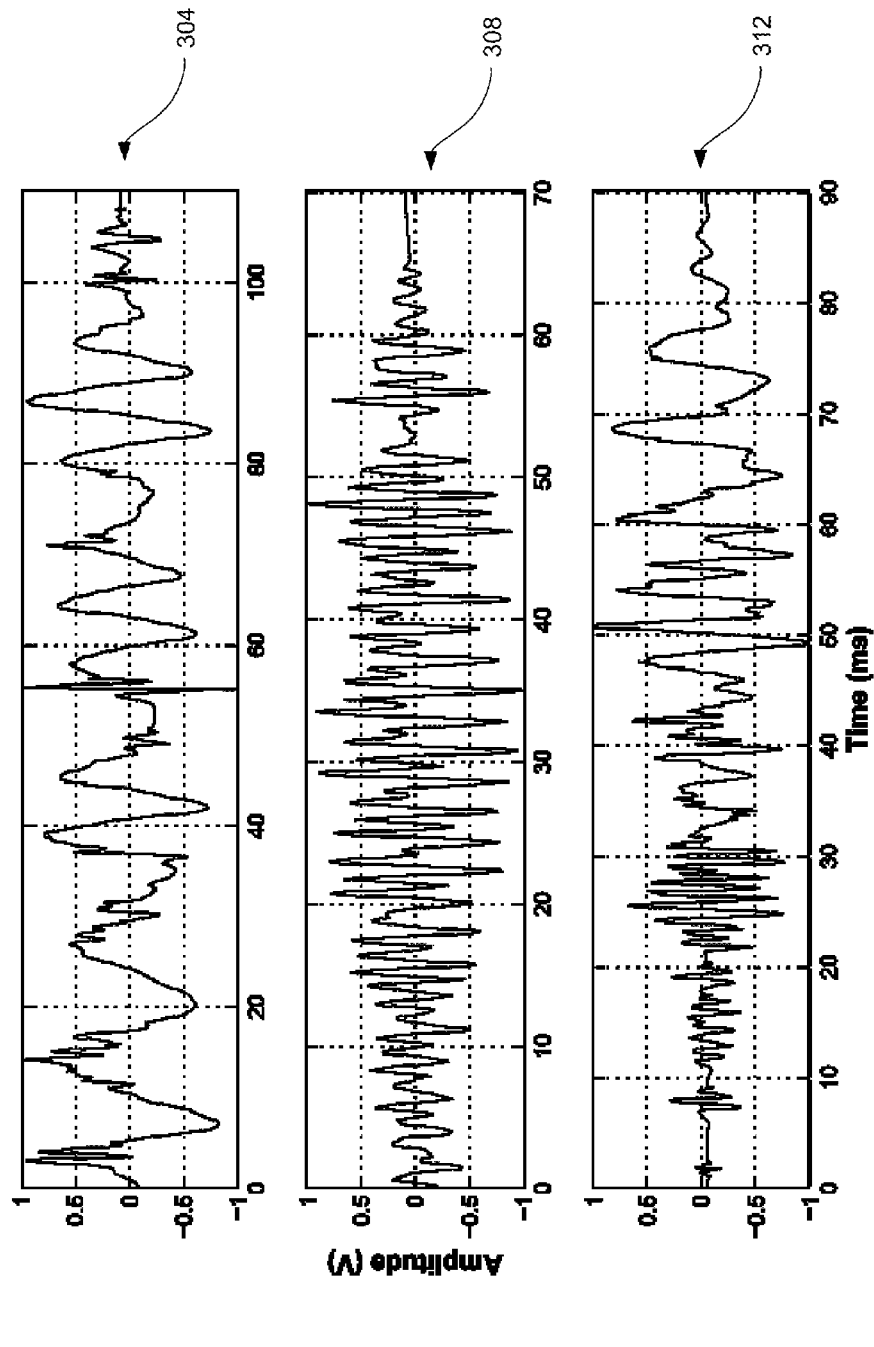
FIG. 3 is a set of graphs showing exemplary signals that can be detected using the apparatus in FIG. 1.

Beginning first at step 210, signals representing swallowing activity are received. When method 200 is implemented using apparatus 30, step 210 refers to the generation of electrical signals by accelerometer 34 and the receipt of those signals at computing device 42. The use of accelerometer 34 means that acceleration signals representing the swallowing activity of patient 38 are received, and due to the unique characteristics of the EMT 25-C accelerometer used in the present embodiment, unique features can be found in the appearance of those signals. FIG. 3 shows examples of signals that can be received using EMT 25-C, indicated generally at 300, and specifically at 304, 308 and 312. Speaking in very general terms, signal 304 is an example of typical pediatric aspiration signals that portray weak or wide-sense stationarity; signal 308 is an aspiration signal that portrays non-stationarity due to evolving variance; and signal 312 is an aspiration signal that portrays nonstationarity due to time-varying frequency and variance structure.

However, it is to be understood that signals 300 are simply raw data, and can represent aspirations or swallows or motion artifact. It has been determined by the inventors that the distribution of median acceleration magnitude is right-skewed for both aspiration and swallows. Due to the skewness of the distribution, gamma distribution is used to estimate the spread and location parameters within signals 300. In particular, the spread a and location b parameters of the gamma distributions for aspirations and swallows that can be associated with signals such as signals 300 are summarized in Table I.

TABLE I

Location and spread of signal accelerations

| Parameter | Aspirations | | Swallows | |
|---|---|---|---|---|
| | Maximum likelihood estimate | 95% confidence interval | Maximum likelihood estimate | 95% confidence interval |
| Spread (a) | 1.3647 g | [0.9343, 1.7952] | 3.642 g | [2.2713, 5.0128] |
| Location (b) | 1.176 g | [0.732, 1.62] | 0.063 g | [0.041, 0.086] |

The stationarity and normality characteristics of signals 300 are summarized in Table II. Stationarity is measured by the nonparametric reverse arrangements tests while normality is measured by a chi-squared distribution-based test of histogram bin counts. Further details about stationarity and normality can be found in "Random Data Analysis and Measurement Procedures" $3^{rd}$ Edition, Julius S. Bendat and Allan G. Pierson, John Wiley & Sons Inc., (c) 2000, New York ("Bendat"), the contents of which are incorporated herein by reference. Chapter 10 of Bendat discusses tests for stationarity, while Chapter 4 of Bendat discusses regarding normality.

Table II thus shows a very general, exemplary, summary of how aspirations and swallows can correspond to the stationarity and normality characteristics of received signals such as signals 300.

TABLE II

Stationarity and normality characteristics of signal accelerations

| | Aspirations | Swallows |
|---|---|---|
| Stationarity | 41% not stationary | 46% not stationary |
| Normality | 90% violating normality | 100% violating normality |

Due to the skewness of the distributions of the bandwidths, a gamma distribution is used to determine the location estimate. The frequency bandwidths can be calculated using a discrete wavelet decomposition at ten levels and determining the level at which the cumulative energy (starting from the final level of decomposition) exceeded 85% of the total energy. This determines the 85% bandwidth for the signal in question.

The location estimate of the about 85% frequency bandwidth can be between about 700 Hz to about 1100 Hz for aspiration signals, and more preferably can be between about 900 Hz and about 950 Hz, and even more preferably between about 910 Hz and about 940 Hz, and still further preferably about 928 Hz for aspiration signals.

The location estimate of the about 85% frequency bandwidth can be between about 400 Hz to about 700 Hz for swallow signals, and more preferably can be between about 500 Hz and about 650 Hz, and even more preferably between about 590 Hz and about 630 Hz, and still further preferably about 613 Hz for swallows.

Having received signals at step 210, method 200 advances to step 220. At step 220, a determination is made as to whether an event is present inside the signals received at step 210. The criteria for making such a determination is not particularly limited. In a present embodiment, when computing device 42 receives a signal magnitude from accelerometer 34 that exceeds an "on" threshold (in a present embodiment of about 0.025 Volts ("V")) for a pre-determined "onset" period (in a present embodiment about thirty milliseconds ("ms")), event initiation is identified and signal recording begins. The next about 12,000 samples are recorded, corresponding to about 1.2 seconds ("s") of data. Back-trimming is then performed to determine when the signal activity substantially ceased. Such back-trimming involves counting the number of data samples below about 0.05 V, starting from the end of the recording. Once this count exceeds about thirty data points, the end of the useful signal is deemed to have been identified and the end of the signal is trimmed therefrom. In a present embodiment, 12000 samples are recorded, but about 15,000 samples (i.e. about 1.5 s of above threshold signal activity) can also be recorded for analysis as a single signal. In other embodiments other numbers of samples can be recorded, as desired. If the foregoing criteria are not met, then it is determined at step 220 that an event has not occurred and method 200 returns to step 210. However, if the criteria is met then method 200 advances from step 220 to step 230, and the signals that are recorded at step 220 is retained for use at step 230.

Next, at step 230, features are extracted from the recorded signals. In a presently preferred embodiment, stationarity, normality and dispersion ratio are three features that are extracted.

In order to extract the stationarity feature, the procedure in Chapter 10 of Bendat is employed. First, the received signal, is divided into non-overlapping bins each of about five milliseconds ("ms") (i.e. for a total of fifty samples) in length. (The received signal can, however, be divided into non-overlapping bins of between about one ms and about nine ms, or more preferably between about three ms and about seven ms.) Where the signal length, defined herein as "L" is not an integral multiple of fifty, the signal was trimmed at the beginning and end of the signal by approximately (L mod 50)/2. Next, the mean square value within each window was computed. Next, the total number of reverse arrangements, referred to herein as $A_{Total}$, in the mean square sequence is determined. Finally, z-deviate serves as the stationarity feature which is determined according to Equation 1.

$$z = \frac{A_{Total} - \mu_A}{\sigma_A} \qquad \text{Equation 1}$$

where:

$\mu_A$ is the mean number of reverse arrangements expected for a stationary signal of the same length.

$\sigma_A$ is the standard deviation for an equal length stationary signal.

In order to extract the normality feature, an adaptation of the procedure in Chapter 4 of Bendat is employed. First, the signal is standardized to have zero mean and unit variance. The standardized signal is referred to herein as "s". Next, the amplitude of the standardized signal, s, is divided into I bins each of about 0.4 Volts, where $$I = \left\lceil \frac{\max(s) - \min(s)}{0.4} \right\rceil.$$

The highest bin extended to infinity and the lowest bin extended to negative infinity.

Next, the observed frequencies n for each bin are determined by counting the number of samples in the standardized signal that fell within each bin. The expected frequencies $\hat{m}$ for each bin is determined under the assumption of normality. The Chi-square statistic was computed as shown in Equation 2.

$$\hat{X}^2 = \sum_{i=1}^{I} \frac{(n_i - \hat{m}_i)^2}{\hat{m}_i} \qquad \text{Equation 2}$$

Finally, the normality feature is computed as shown in Equation 3.

$$\log_{10}(\hat{X}^2) \qquad \text{Equation 3}$$

In order to determine the dispersion ratio feature, the mean absolute deviation of each signal is determined according to Equation 4.

$$S_1 = \frac{1}{n} \sum_{i=1}^{n} |x_i - med(x)|. \qquad \text{Equation 4}$$

Next, the interquartile range, $S_2$, of each signal is determined. The interquartile range is defined in Chapter 2 of "Introduction to robust estimation and hypothesis testing", R and R. Wilcox, 1997, Academic Press, CA. Finally, the dispersion ratio feature is determined according to Equation 5.

$$\frac{S_1}{S_2} \qquad \text{Equation 5}$$

Having extracted these features from the signal, method 200 advances to step 240, at which point the signal is classified based on the features extracted at step 230. In a presently preferred embodiment, the classification is performed using a radial basis function neural network implemented on the microcontroller of device 42 to classify swallowing events in real-time, as either swallows or aspirations. Further details about such a radial basis function neural network can be found in Chapter 5 of "Neural Networks for Pattern Recognition", Christopher Bishop, 1995, Clarendon Press, Oxford ("Bishop"), the contents of which are incorporated herein by reference. The network is operable to take the three extracted features as inputs, and output a single number as its classification of the detected type of swallowing activity. In particular, an output level of about 0.1 is assigned to represent swallows and an output level of about 0.9 to represent aspirations. The network architecture consists of three inputs corresponding to each extracted feature, eighty-nine radial basis function units determined from an interactive training procedure as outlined in "Bishop" and one output unit, representing swallowing or aspiration. While eighty-nine radial basis units is presently preferred, in other embodiments from about seventy-five to about one-hundred radial basis units can be used, and in other embodiments from about eighty to about ninety-five radial basis units can be used, all corresponding to one output. The first layer is nonlinear and the second layer is linear. Put in other words, the first layer of the network consists of the nonlinear radial basis functions while the second layer of the network is a weighted linear summation of the radial basis function outputs.

Figure 4:
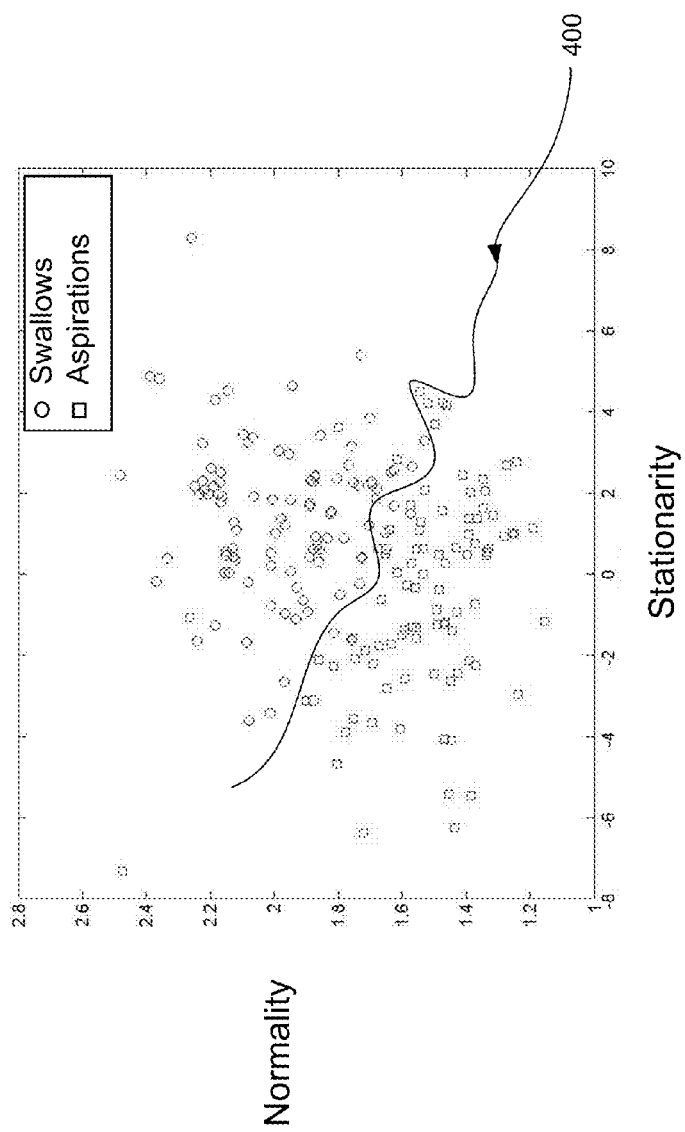
FIG. 4 is a graph showing exemplary output that can be generated by the method in FIG. 2.

Referring now to FIG. 4, a scatter plot is shown for the results of performing steps 210-240 for a number of different signals. The scatter plot in FIG. 4 is only two dimensional, showing only a plot of the stationarity features vs. the normality features. It can be seen that the squares on the scatter plot indicate where aspirations actually occurred, whereas the circles indicate swallows actually occurred. The scatter plot was generated while performing method 200 in conjunction with videofluroscopy so that the actual swallowing activity could be verified, not withstanding the classification performed at step 230, so that the classifications made at step 230 could be verified for accuracy. The line indicated at 400 in FIG. 4 represents a rough dividing line between classifications associated with swallows and aspirations. While some measurements in the scatter plot show a classification that does not reflect the actual type of swallowing activity, the majority of swallowing events are in fact correctly classified. Further improvement to the results shown in FIG. 4 are obtained when the third feature, dispersion ratio, is used to assist in the determination.

Method 200 then advances to step 250, at which point an output is generated corresponding to the classification performed at step 240. Thus, where a particular event was classified as a swallow, then display 54 of device 42 would be instructed to present the message "SWALLOW", whereas if the event was classified as an aspiration then display 54 of device 42 would be instructed to present the message "ASPIRATION". Such messages presented by device 42 could also include colours (e.g. green associated with swallows, red associated with aspirations) and/or auditory signals (e.g. no sound for swallow, beeping for aspirations).

Using method 200, an individual feeding patient 38 can adjust how the feeding is being performed in order to reduce aspirations and increase swallows. Such adjustments to feedings can be based on changing consistency or type of food, the size and/or frequency of mouthfuls being offered to patient 38, and the like.

It should now be understood that as method 200 is implemented using device 42, the microcontroller of device 42 will be provided with software programming instructions corresponding to method 200.

While only specific combinations of the various features and components of the present invention have been discussed herein, it will be apparent to those of skill in the art that desired subsets of the disclosed features and components and/or alternative combinations of these features and components can be utilized, as desired. For example, it is also to be understood that other types of vibration sensors other than accelerometer 34 can be used with appropriate modifications to computing device 42. While presently less preferred, another sensor can include a sensor that measure displacement (e.g microphone), while having computing device 42 record received displacement signals over time. Another type of sensor can include a sensor that measures velocity, having computing device 42 record received velocity signals over time. Such signals can then be converted into acceleration signals and processed according to the above, or other techniques of feature extraction and classification thereof that work with the type of received signal can be employed, as desired.

As an additional example, while at step 230 of method 200 stationarity, normality and dispersion ratio are three features that are extracted, it is to be understood that in other embodiments other features and/or combinations thereof can be extracted that can be used to detect a swallowing event. For example, while presently less preferred, it can be desired to simply extract any two of stationarity, normality and dispersion ratio in order to make a determination as to whether a particular swallowing event is to be classified as a swallow or aspiration.

Furthermore, while computing device 42 is a personal digital assistant having a programmable microprocessor and display, in other embodiments device 42 can simply be an electronic device that includes circuitry dedicated to processing signals from an accelerometer (or other sensor) and classifying those signals as different types of swallowing activity. Similarly, the device can simply include a set of indicator lights—e.g. a pair of indicator lights, one light for indicating a swallow, the other for indicating an aspiration. Whatever the format of device 42, device 42 can also include an interface for connection to a personal computer or other computing device so that updated programming instructions for detecting aspirations, swallows and/or other types of swallowing activity can be uploaded thereto.

The above-described embodiments of the invention are intended to be examples of the present invention and alterations and modifications may be effected thereto, by those of skill in the art, without departing from the scope of the invention which is defined solely by the claims appended hereto.

The invention claimed is:

1. A method for detecting an aspiration of foodstuff wherein aspiration is the entry of foreign material into the airway during inspiration, the method comprising:
   providing criteria for differentiating between activity related to an aspiration of foodstuff and activity related to a swallow of foodstuff;
   positioning at least one sensor externally on a throat of a subject;
   providing foodstuff to the subject;
   receiving from the at least one sensor an electronic signal corresponding to throat vibrations associated with an intake of foodstuff;
   extracting at least two features from the electronic signal;
   classifying the at least two extracted features according to the criteria for differentiating between activity related to the aspiration of foodstuff and activity related to the swallow of foodstuff; and
   generating an output representing one of:
      an aspiration of foodstuff; and
      a swallow.

2. The method of claim 1, wherein the foodstuff is at least one of a liquid foodstuff, a solid foodstuff, and a semi-solid foodstuff.

3. The method of claim 1 wherein the at least two extracted features include at least two of stationarity, normality and dispersion ratio.

4. The method of claim 1 wherein the classifying the extracted features according to the criteria for differentiating between activity related to the aspiration of foodstuff and activity related to the swallow of foodstuff includes using a radial basis neural network.

5. The method of claim 1 wherein the extracting at least two features from the electronic signal includes extracting a stationarity feature (z), and the method further comprises:
   dividing the electronic signal into a plurality of non-overlapping bins;
   determining a total number of reverse arrangements, ($A_{Total}$) in a mean square sequence; and
   extracting the stationarity feature (z), determined according to the following equation:

$$z = \frac{A_{Total} - \mu_A}{\sigma_A}$$

where:
$\mu_A$ is a mean number of reverse arrangements expected for a stationary signal of a same length; and
$\sigma_A$ is a standard deviation for an equal length stationary signal.

6. The method of claim 5 wherein each of the plurality of non-overlapping bins has a length between about one millisecond and about nine milliseconds.

7. The method of claim 5 wherein each of the plurality of non-overlapping bins has a length between about three milliseconds and about seven milliseconds.

8. The method of claim 5 wherein each of the plurality of non-overlapping bins has a length of about five milliseconds.

9. The method of claim 1 wherein the extracting at least two features from the electronic signal includes extracting a normality feature, and the method further comprises:
   standardizing the electronic signal to have zero mean and unit variance ("s");
   dividing the standardized electronic signal into a plurality of bins ("I") of about 0.4 Volts each, where $$I = \left\lceil \frac{\max(s) - \min(s)}{0.4} \right\rceil,$$

and wherein a highest bin extends to infinity and a lowest bin extends to negative infinity;
   determining observed frequencies ("n") for each bin by counting a number of samples in the standardized electronic signal ("s") that fell within each bin;

determining expected frequencies ("m̂") for each bin under an assumption of normality, using a Chi-square ($X^2$) statistic of:

$$\hat{X}^2 = \sum_{i=1}^{I} \frac{(n_i - \hat{m}_i)^2}{\hat{m}_i}; \text{ and}$$

determining the normality feature using the following equation:

$$\log_{10}(\hat{X}^2).$$

10. The method of claim 1 wherein the extracting at least two features from the electronic signal includes extracting a dispersion ratio, and the method further comprises:
determining a mean absolute deviation ("$S_1$") of the electronic signal according to the following equation:

$$S_1 = \frac{1}{n}\sum_{i=1}^{n}|x_i - med(x)|$$

determining an interquartile range ("$S_2$"), of the electronic signal; and
extracting the dispersion ratio according to the following equation:

$$\frac{S_1}{S_2}.$$

11. A device for detecting aspiration of foodstuff wherein aspiration is the entry of foreign material into the airway during inspiration comprising:
at least one sensor configured to be positioned externally on a throat of a subject and detect throat vibrations associated with an intake of foodstuff; and
a computing device configured to receive an electronic signal from the at least one sensor corresponding to the throat vibrations, extract at least two features from the electronic signal, determine whether the extracted features meet predefined criteria for an aspiration of foodstuff, and generate an output representing one of:
an aspiration of foodstuff, and
a swallow.

12. The device of claim 11, wherein the foodstuff is at least one of a liquid foodstuff, a solid foodstuff, and a semi-solid foodstuff.

13. The device of claim 11, wherein the computing device is further configured to differentiate between an aspiration of foodstuff and a swallow of foodstuff.

14. The device of claim 11 wherein the at least one sensor is an accelerometer.

15. The device of claim 11 wherein the extracted features include at least two of stationarity, normality and dispersion ratio.

16. The device of claim 11 wherein the computing device employs a radial basis neural network to classify the electronic signal.

17. The device of claim 11 wherein the computing device is further configured to:
divide the electronic signal into a plurality of non-overlapping bins;

determine a total number of reverse arrangements, ($A_{total}$) in a mean square sequence; and
extract a stationarity feature (z), determined according to the following equation:

$$z = \frac{A_{Total} - \mu_A}{\sigma_A}$$

where:
$\mu_A$ is a mean number of reverse arrangements expected for a stationary signal of a same length; and
$\sigma_A$ is a standard deviation for an equal length stationary signal.

18. The device of claim 11 wherein the computing device is further configured to:
standardize the electronic signal to have zero mean and unit variance ("s");
divide the standardized electronic signal into a plurality of bins ("I") each of about 0.4 Volts, where $$I = \frac{\lceil \max(s) - \min(s) \rceil}{0.4},$$

and wherein a highest bin extends to infinity and a lowest bin extends to negative infinity;
determine observed frequencies ("n") for each bin by counting a number of samples in the standardized electronic signal ("s") that fell within each bin;
determine expected frequencies ("m̂") for each bin under an assumption of normality, using a Chi-square ($X^2$) statistic of:

$$\hat{X}^2 = \sum_{i=1}^{I} \frac{(n_i - \hat{m}_i)^2}{\hat{m}_i}; \text{ and}$$

determine a normality feature using the following equation:

$$\log_{10}(\hat{X}^2).$$

19. The device of claim 11 wherein the computing device is further configured to:
determine a mean absolute deviation of the electronic signal according to the following equation:

$$S_1 = \frac{1}{n}\sum_{i=1}^{n}|x_i - med(x)|$$

determine an interquartile range $S_2$, of the electronic signal; and
extract a dispersion ratio according to the following equation:

$$\frac{S_1}{S_2}.$$

20. The device of claim 11, further comprising a wired link having at least two ends, including a first end connected to the at least one sensor and a second end connected to the computing device.

21. The device of claim 11, wherein the computing device is configured to wirelessly receive the electronic signal from the at least one sensor.

22. A method of analyzing a signal from a sensor configured to be placed externally on a throat of a subject to determine whether the subject is aspirating during intake of foodstuff, the method comprising:
providing criteria for an aspiration wherein aspiration is the entry of foreign material into the airway during inspiration;
receiving a signal from the sensor;
extracting at least two statistical features from the signal;
determining whether the at least two statistical features meet the criteria for an aspiration; and
generating an output an representing one of:
an aspiration of foodstuff, and
a swallow of foodstuff.

23. The method of claim 22 wherein the providing criteria for an aspiration includes providing criteria for differentiating between activity related to an aspiration of foodstuff and activity related to a swallow of foodstuff.

24. The method of claim 22 wherein the extracting at least two features from the electronic signal includes extracting stationarity, and the method further comprises:
dividing the electronic signal into a plurality of non-overlapping bins;
determining a total number of reverse arrangements, ($A_{Total}$) in a mean square sequence; and
extracting a stationarity feature (z), determined according to the following equation:

$$z = \frac{A_{Total} - \mu_A}{\sigma_A}$$

where $\mu_A$ is a mean number of reverse arrangements expected for a stationary signal of a same length and $\sigma_A$ is a standard deviation for an equal length stationary signal.

25. The method of claim 22 wherein the extracting at least two features from the electronic signal includes extracting normality, and the method further comprises:
standardizing the electronic signal to have zero mean and unit variance ("s");
dividing the standardized electronic signal into a plurality of bins ("I") of about 0.4 Volts each, where $$I = \left\lceil \frac{\max(s) - \min(s)}{0.4} \right\rceil,$$

and wherein a highest bin extends to infinity and a lowest bin extends to negative infinity;
determining observed frequencies ("n") for each bin by counting a number of samples in the standardized electronic signal ("s") that fell within each bin;
determining expected frequencies ("m̂") for each bin under an assumption of normality, using a Chi-square ($X^2$) statistic of:

$$\hat{X}^2 = \sum_{i=1}^{I} \frac{(n_i - \hat{m}_i)^2}{\hat{m}_i}; \text{ and}$$

determining a normality feature using the following equation:

$$\log_{10}(\hat{X}^2).$$

26. The method of claim 22 wherein the extracting at least two features from the electronic signal includes extracting dispersion ratio, and the method further comprises:
determining a mean absolute deviation ("$S_1$") of the electronic signal according to the following equation:

$$S_1 = \frac{1}{n}\sum_{i=1}^{n} |x_i - med(x)|$$

determining an interquartile range ("$S_2$"), of the electronic signal; and
extracting a dispersion ratio according to the following equation:

$$\frac{S_1}{S_2}.$$

* * * * *